United States Patent
Tachibana et al.

(10) Patent No.: US 6,821,306 B2
(45) Date of Patent: Nov. 23, 2004

(54) METHOD FOR PRODUCING MIXED CRYSTALS OF DISODIUM 5'-GUANYLATE AND DISODIUM 5'-INOSINATE

(75) Inventors: Shinya Tachibana, Kawasaki (JP); Yasuo Yonou, Kawasaki (JP); Naoto Hirano, Kawasaki (JP); Shigemitsu Abe, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 456 days.

(21) Appl. No.: 10/098,405

(22) Filed: Mar. 18, 2002

(65) Prior Publication Data

US 2002/0177702 A1 Nov. 28, 2002

(30) Foreign Application Priority Data

Mar. 26, 2001 (JP) .................................... 2001-086563

(51) Int. Cl.$^7$ ................................................ B01D 9/00
(52) U.S. Cl. ..................................... 23/295 R; 23/300
(58) Field of Search ............................. 23/295 R, 300, 23/299, 307

(56) References Cited

U.S. PATENT DOCUMENTS 4,775,546 A * 10/1988 Higurashi et al. .......... 426/649

* cited by examiner

Primary Examiner—Stanley S. Silverman
Assistant Examiner—Edward M. Johnson
(74) Attorney, Agent, or Firm—Oblon, Spivak, McClelland, Maier & Neustadt, P.C.

(57) ABSTRACT

Herein is disclosed a method for producing mixed crystals of disodium 5'-guanylate and disodium 5'-inosinate which comprises feeding a mixed solution of disodium 5'-guanylate and disodium 5'-inosinate which solution will become supersaturated at the below-mentioned constant temperature, to a solution or slurry of disodium 5'-guanylate and disodium 5'-inosinate charged in a crystallization bath (lower-temperature bath) and kept at a constant temperature, whereby mixed crystals of disodium 5'-guanylate and disodium 5'-inosinate are deposited from the mixed solution of disodium 5'-guanylate and disodium 5'-inosinate, according to which method 5'-GMP2Na which is difficult to handle due to the properties and powder characteristic of its crystals in particular and 5'-IMP2Na, in the form of crystals which are easy to handle, that is, I+G mixed crystals having a given I/G ratio, can be produced under simple process control and with inexpensive facilities, with the I/G ratio being controlled easily.

2 Claims, 2 Drawing Sheets

1

METHOD FOR PRODUCING MIXED CRYSTALS OF DISODIUM 5'-GUANYLATE AND DISODIUM 5'-INOSINATE

BACKGROUND OF THE INVENTION

1. Technical Field of the Invention

The present invention relates to a remarkably improved method for producing disodium 5'-guanylate (i.e., 5'-guanylic acid disodium salt, being hereinafter often abbreviated as "5'-GMP2Na") and disodium 5'-inosinate (i.e., 5'-inosinic acid disodium salt, being hereinafter often abbreviated as "5'-IMP2Na"), both being known to be important as seasonings, drugs and the like in the form of mixed crystals, not a mere mixture thereof.

2. Related Art

5'-GMP2Na and 5'-IMP2Na, as has been described above, are important in the fields of seasonings or condiments, drugs and the like. However, when they need to be used in combination, it is extremely difficult to prepare a mixture with a given mixed ratio by simply powder-mixing their crystals together, due to differences in the properties and powder characteristics of the two kinds of crystals. In addition, handling of such a mixture involves a variety of difficulties.

Meanwhile, there have been known as methods for producing 5'-GMP2Na and 5'-IMP2Na in the form of mixed crystals, the following three methods: I.e., a 1st one is a method (as disclosed in Japanese Patent Publication No. 12914/1965) comprising the steps of dissolving 5'-GMP2Na and 5'-IMP2Na in an aqueous solution containing an organic solvent such as methanol or the like and obtaining mixed crystals (being hereinafter often abbreviated as "I+G mixed crystals") of 5'-GMP2Na and 5'-IMP2Na from the resulting solution, a 2nd one is a method (as disclosed in Japanese Patent Publications Nos. 16582/1979 and 4787/80) comprising the steps of dissolving 5'-GMP2Na and 5'-IMP2Na in water and obtaining I+G mixed crystals from the resulting solution by means of crystallization by cooling or concentrating, and a 3rd one is a method (as disclosed in Japanese Patent Publication No. 215494/1991 and Japanese Patent No. 2,770,470) in which a 5'-IMP2Na-containing aqueous solution is gradually added to a 5'-GMP2Na slurry solution at precipitating 5'-GMP2Na, whereby I+G mixed crystals are formed.

Incidentally, 5'-GMP2Na and 5'-IMP2Na are known to form a mixed crystal in such a manner that 5'-GMP2Na is incorporated into a crystal lattice of 5'-IMP2Na in an aqueous solution containing an organic solvent such as methanol or the like or a mere aqueous solution. An X-ray diffraction pattern of the mixed crystal is almost the same as that of 5'-IMP2Na. It is considered that 5'-GMP2Na having a similar chemical structure to that of 5'-IMP2Na enters a lattice of 5'-IMP2Na, and they maintain a stable condition by means of hydrogen bonding. A crystal of 5'-IMP2Na has a good crystal form, and an I+G mixed crystal having the same lattice has almost the same crystal form.

In order to obtain I+G mixed crystals by crystallization, although the above 1st method can achieve crystallization at a high recovery rate, it has the problem that it requires expensive explosion-proof facilities on an industrial scale because it uses an organic solvent, and therefore production costs increase. Further, in order to obtain a product (mixed crystals) having a desirable weight ratio of 5'-IMP2Na to 5'-GMP2Na (being hereinafter often abbreviated as "I/G ratio") by the above 2nd method, concentrated drains and feed liquids must be controlled, and conditions for setting temperatures, pressures and like must be strictly controlled in the case of crystallization by concentrating, while in the case of crystallization by cooling, the composition of a crystallization solution (i.e., a solution (to be) subjected to crystallization) must be controlled more strictly because the composition of the crystallization solution tends to change continuously, and therefore, both cases have the problem that devices and control of processes become complicated. In the case of the above 3rd method, the starting raw materials, 5'-IMP2Na and 5'-GMP2Na, must be kept separate from each other, and there is the problem that the number of facilities increases in order to prevent 5'-IMP2Na and 5'-GMP2Na from mixing with each other before crystallization.

SUMMARY OF THE INVENTION

Problems to be Solved by the Invention

It is an object of the present invention to provide a method for producing 5'-GMP2Na which is difficult to handle due to the properties and powder characteristic of its crystals in particular and 5'-IMP2Na, in the form of crystals which are easy to handle, that is, I+G mixed crystals having a given I/G ratio, under simple process control and with inexpensive facilities with the I/G ratio being controlled easily.

Means to Solve the Problem

The present inventors have made extensive and intensive studies to improve conventionally known crystallization methods of I+G mixed crystals, which methods involve complicated or intricate control and processes. Consequently, they have found that I+G mixed crystals with a given I/G ratio and stable quality can be deposited or precipitated by carrying out crystallization under constant temperature conditions that are industrially easy to control, more specifically, that the above object can be achieved by feeding a mixed feed solution of 5'-IMP2Na and 5'-GMP2Na with a high concentration which will become supersaturated at the temperature of the solution charged in the below-described crystallization bath (in the present specification, the term "charged solution" or "solution charged" is used in such a sense that it includes "charged slurry" or "slurry charged" (in the broad sense)) into the crystallization bath (lower-temperature bath) kept at a constant temperature which is lower than the temperature of the mixed feed solution, whereby I+G mixed crystals are deposited from the mixed solution of 5'-IMP2Na and 5'-GMP2Na due to the difference in solubility which is, in turn, ascribable to the difference in temperature. The present invention has been completed based on these findings.

Accordingly, the present invention relates to a method for producing mixed crystals of disodium 5'-guanylate and disodium 5'-inosinate which comprises feeding a mixed solution of disodium 5'-guanylate and disodium 5'-inosinate which solution will become supersaturated at the below-mentioned constant temperature, to a solution or slurry of disodium 5'-guanylate and disodium 5'-inosinate charged in a crystallization bath (lower-temperature bath) and kept at a constant temperature, whereby mixed crystals of disodium 5'-guanylate and disodium 5'-inosinate are deposited from the mixed solution of disodium 5'-guanylate and disodium 5'-inosinate.

DETAILED DESCRIPTION OF THE INVENTION

Figure 1:
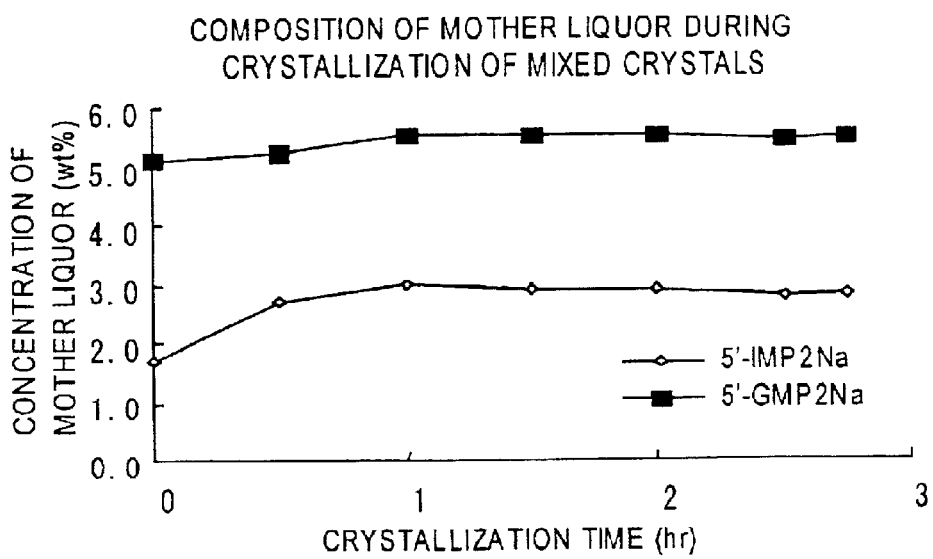
FIG. 1 gives a diagram showing the change of composition of a mother liquor during crystallization of mixed crystals (Example 1).

The present invention will be described in detail hereinafter.

Firstly, a mixed solution (mixed feed solution) of 5'-IMP2Na and 5'-GMP2Na to be used as a feed solution according to the production method of the present invention will be described.

This feed solution can be prepared not only from product crystals of 5'-IMP2Na and those of 5'-GMP2Na using water or an aqueous solution containing an organic solvent as a solvent but also from, for example, I+G mixed crystals having an I/G ratio out of a predetermined range or crude crystals of 5'-IMP2Na and those 5'-GMP2Na in the course of production process by means of a method such as a fermentation method, organic synthesis method or the like. However, it is needless to say that the amount of the impurities is limited to such degree that they do not affect the solubility or crystal growth rate of target I+G mixed crystals. The proportion of the 5'-IMP2Na and the 5'-GMP2Na in a dissolved solution (mixed feed solution) can be set arbitrarily within a range of 5 to 40% in accord with the I/G ratio of the target I+G mixed crystals, and is preferably 8 to 25%. Further, the concentrations of 5'-IMP2Na and 5'-GMP2Na in a mixed feed solution need to be at least equal to the common solubility of 5'-IMP2Na and 5'-GMP2Na at a set temperature of the lower-temperature bath. Furthermore, in order to obtain I+G mixed crystals having an I/G ratio of 1.0, the I/G ratio of the dissolved solution must fall within a range of 0.82 to 0.95.

In addition, it is effective in improving a crystallization yield to add about 5 to 20%, preferably about 8 to 15%, based on solubility, of a salt such as NaCl, $Na_2SO_4$, $(NH_4)_2SO_4$, $NH_4Cl$, $Na_2HPO_4$ or the like to a mixed feed solution and carry out crystallization where the solubility of each component of the target mixed crystals is low due to the salting-out effects by these salts.

Next, a solution or slurry charged in a lower-temperature bath and kept at a constant temperature which is lower than that of a mixed feed solution to cause the mixed feed solution to become supersaturated so as to deposit I+G mixed crystals, will be described.

As such a charged solution or charged slurry, there may be mentioned a crystallization slurry which has been prepared from the same mixed solution as the feed solution, a mixed solution of 5'-IMP2Na and 5'-GMP2Na which has been prepared by use of water, an aqueous solution containing an organic solvent, or the like, as the solvent, and the like. Although the composition thereof is not particularly limited, a slurry of I+G mixed crystals having an I/G ratio of 0.8 to 1.5, having a slurry concentration of about 10 to 20% (ratio indicated in % of the amount of mixed crystals of 5'-IMP2Na and 5'-GMP2Na (solid) to the amount of the mixed solution inclusive of the solid mixed crystals), and having a temperature of about 30 to 50° C., is preferred, in consideration of improving the physical properties of I+G mixed crystals obtained by feeding a mixed feed solution, as compared with those of each component of I+G mixed crystals, particularly 5'-GMP2Na, and securing stability in controlling the I/G ratio. The amount of the slurry is preferably about 10 to 30% based on the amount of the feed solution to be added. As a method for preparing such a slurry, there may be employed any crystallization method such as cooling crystallization, concentrating crystallization, crystallization involving addition of an auxiliary (such as an inorganic salt, an organic solvent, or the like) or the like. In every case, although a slurry may be formed by spontaneous crystallization, it is preferably prepared by adding, as seed crystals, 5'-IMP2Na crystals or I+G mixed crystals in an amount of about 5 to 20% based on the total amount of the 5'-IMP2Na and 5'-GMP2Na present in the charged solution. Further, such a slurry may be also prepared by adding existing 5'-IMP2Na crystals or I+G mixed crystals into water in an amount exceeding the solubility thereof, without resorting to crystallization. Incidentally, 5'-GMP2Na crystals are not appropriate as seed crystals due to the properties and powder characteristics of the crystals.

A solution or slurry charged in a lower-temperature bath must be kept at a constant temperature. Thereby, the composition of the mother solution becomes stable in the course of crystallization, and I+G mixed crystals deposited during the crystallization has a fixed I/G ratio, accordingly.

Finally, crystallization manipulations will be described.

As for a pH at which crystallization is carried out, when it is within a pH range of each disodium salt of 5'-IMP2Na and 5'-GMP2Na, i.e., a pH range of 6 to 10, on the phase diagram, I+G mixed crystals can be obtained. It is preferred that the feed solution and charged solution or charged slurry have all a pH of about 6 to 8.

Upon feeding a feed solution into a lower-temperature bath, it is preferably added as slowly as possible, preferably over a period of three hours, whereby crystals deposited by growth of seed crystals or spontaneous crystallization in the bath are kept in good shape. Further, it is also preferable that stirring be maintained in good condition so that the fed solution can be diffused quickly.

After completion of feed of the feed solution, solid-liquid separation can be performed directly. However, it is also possible to carry out a cooling operation to some extent, whereby the yield is improved. In this case as well, about 80% of the deposited crystals has been deposited in the course of feeding, and the I/G ratio of the I+G mixed crystals becomes more stable than when cooling crystallization is carried out from the start.

EXAMPLES

The present invention will be further described with reference to examples hereinafter.

Example 1

No Seed Crystals Added, Constant Temperature Feed-Type Crystallization 63 g of an aqueous solution containing 1.1 g of 5'-IMP2Na, 3.2 g of 5'-GMP2Na and 6.5 g of NaCl was kept at 40° C. as a charged solution. 520 g of feed solution containing 52 g of 5'-IMP2Na, 64 g of 5'-GMP2Na and 52 g of NaCl was added to the charged solution over a period of three hours with stirring. As for the composition of the mother solution during addition, the concentration of 5'-IMP2Na increased at the initial stage but the composition of the mother solution was kept constant thereafter (FIG. 1).

After completion of the addition, the resulting slurry was cooled to 30° C., the crystals were separated by centrifuging, and the separated crystals (mixed crystals) were then dried. Solid-liquid separability at the time of separating the crystals was good.

Figure 2:
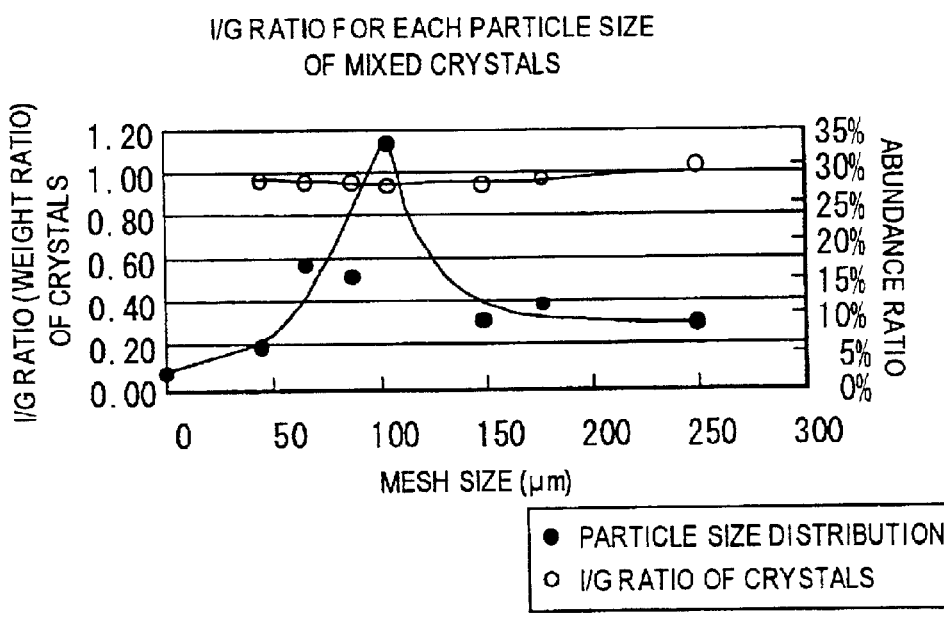
FIG. 2 gives a diagram showing I/G ratios for various particle size levels of the mixed crystals (Example 1).

The I/G ratios of the mixed crystals having different particle diameters were almost the same throughout the various particle size levels (FIG. 2). That is, the dried crystals were sieved by use of sieves having a mesh size of 44, 66, 88, 105, 149, 177 and 250 μm (In FIG. 2, size of particles passing through a sieve having a mesh size of 44 μm is indicated as 0 μm). After sieving, the I/G ratio of each sieved fraction of the crystals was measured. As a result, the I/G ratios were almost the same throughout all the fractions.

Comparative Example 1

No Seed Crystals Added, Cooling Crystallization

After 575 g of an aqueous solution containing 67 g of 5'-IMP2Na, 74 g of 5'-GMP2Na and 57 g of NaCl was cooled from 65° C. to 30° C. over a period of 5 hours, the crystals were separated by centrifuging, and the separated crystals were dried.

Figure 3:
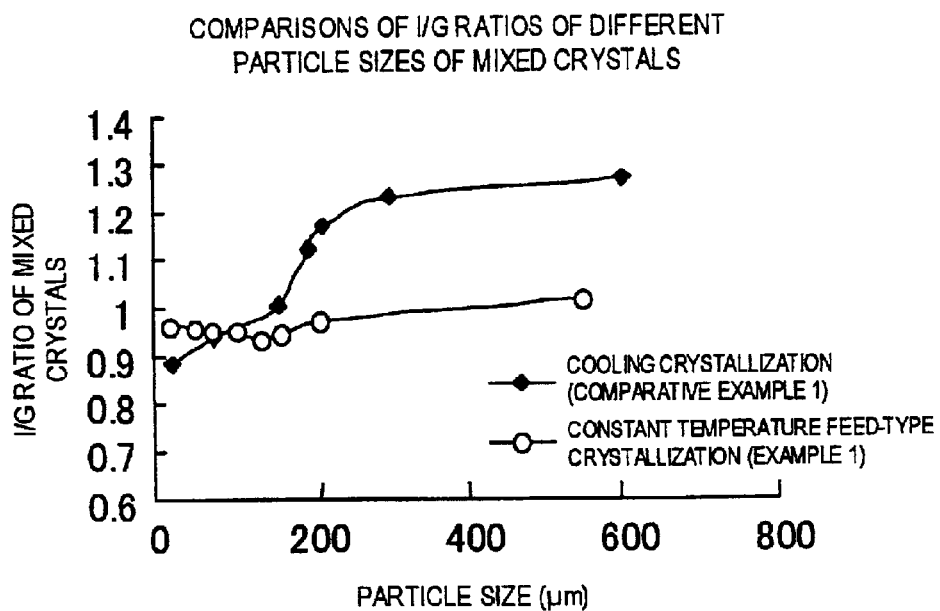
FIG. 3 gives a diagram showing I/G ratios for various particle size levels of mixed crystals (Comparative Example 1).

The I/G ratios of the dried crystals having different particle diameters were measured and compared with the I/G ratios of the crystals obtained in Example 1 (FIG. 3). That is, the two kinds of dried crystals, i.e., those obtained in Comparative Example 1 and those obtained in the same manner as in Example 1, were respectively sieved by use of sieves having a mesh size of 53, 106, 180, 215, 250 and 355 μm (In FIG. 3, size of particles passing through a sieve having a mesh size of 53 μm is indicated as 0 μm). After sieving, the I/G ratio of each sieved fraction of the two kind of crystals was measured. As a result, unlike in the case of the constant temperature feed-type crystallization of Example 1, the I/G ratios of the crystals obtained by cooling crystallization of Comparative Example 1 were significantly different between the crystals having different particle diameters.

From the above results of Example 1 and Comparative Example 1, it was confirmed that the method of the present invention is a crystallization method which is capable of carrying out stable crystallization easily under given conditions and facilitating control of the composition (I/G ratio) of an I+G mixed crystal.

Example 2

No Seed Crystals Added, Constant Temperature Feed-Type Crystallization at Varied Temperatures 63 g of an aqueous solution containing 1.1 g of 5'-IMP2Na, 3.2 g of 5'-GMP2Na and 6.5 g of NaCl was kept at 30, 40 or 50° C. as a charged solution. 520 g of feed solution containing 52 g of 5'-IMP2Na, 64 g of 5'-GMP2Na and 52 g of NaCl was added to the charged solution over a period of four hours with stirring. After completion of the addition, the crystals were separated by centrifuging, with the resulting slurry kept at the feed temperature, and the separated crystals were dried.

Figure 4:
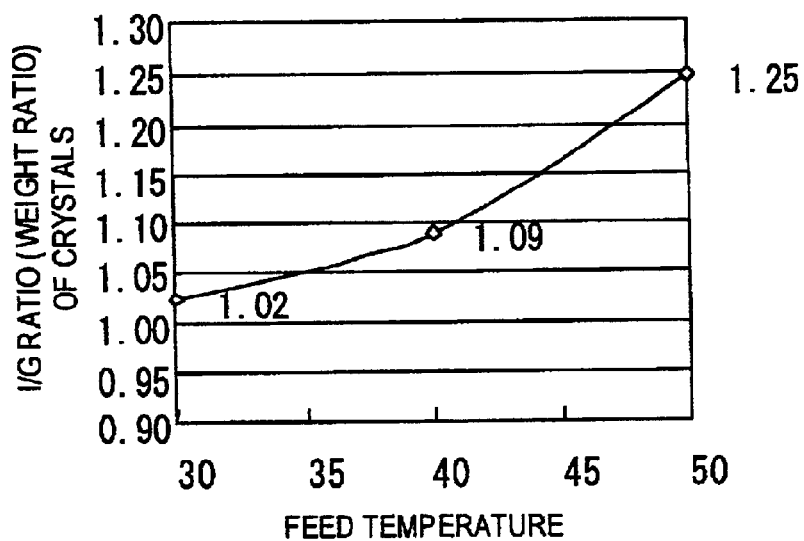
FIG. 4 gives a diagram showing the relationship between a feed temperature and an I/G ratio of deposited mixed crystals (Example 2).

The I/G ratios of the three kinds of dried crystals were measured (FIG. 4). It is understood from FIG. 4 that mixed crystals having a target I/G ratio can be obtained easily by controlling the temperature.

Example 3

No Seed Crystals Added and Seed Crystals Added (Charged Slurry Used)

65 g of a charged solution containing 7.6 g of 5'-IMP2Na, 8.5 g of 5'-GMP2Na and 6.5 g of NaCl was subjected to crystallization by cooling to 40° C. directly (no seed crystals added) or before 4 g of I+G mixed crystals or 5'-IMP2Na crystals was added thereto as seed crystals, whereby a charged slurry was formed. 575 g of feed solution containing 67 g of 5'-IMP2Na, 74 g of 5'-GMP2Na and 57 g of NaCl was added to the charged slurry over a period of four hours with stirring. After completion of the addition, the slurry was cooled to 30° C. Thereafter, the crystals were separated by centrifuging and the separated crystals were dried.

The powder characteristics (rough specific volume and angle of repose) of the three kinds of crystals obtained are shown in the following table 1.

TABLE 1

Effect of Adding Seed Crystals

| Seed Crystals | Rough Specific Volume | Angle of Repose (°) |
| --- | --- | --- |
| Not Added | 1.9 | 49 |
| I + G Mixed Crystals | 1.6 | 46 |
| IMP(*) | 1.4 | 43 |

(*)IMP indicates crystals of 5'-inosinic acid disodium salt.

From the above results of Example 3, it was confirmed that addition of seed crystals improves powder characteristics.

Example 4

Seed Crystals Used—Charged Slurry Used

A feed solution having a composition shown in the following table 2 was continuously added with stirring over a period of 4 hours, to a charged slurry (crystals deposited in situ and contained in the slurry serving as seed crystals) obtained by subjecting a solution having the same composition to crystallization by cooling to 40° C. in each run. After completion of the addition, the slurry was cooled to 30° C., the crystals were separated by centrifuging, and the separated crystals were dried.

TABLE 2

Relationship between Composition of Feed Solution and Composition of I + G Mixed Crystals

| Run No. | Composition of Feed Solution(*1) | | | Composition of Deposited Crystals |
| --- | --- | --- | --- | --- |
|  | IMP(*2) | GMP(*3) | I/G ratio | I/G ratio |
| 1 | 9.9 | 12.2 | 0.81 | 0.89 |
| 2 | 9.7 | 11.5 | 0.84 | 1.02 |
| 3 | 10.6 | 11.6 | 0.91 | 1.03 |
| 4 | 10.2 | 11.1 | 0.92 | 1.04 |
| 5 | 9.1 | 12.8 | 0.71 | 0.87 |
| 6 | 12.1 | 9.8 | 1.23 | 1.88 |

(*1)All feed solutions each contained 10% of NaCl.
(*2)IMP indicates 5'-inosinic acid disodium salt.
(*3)GMP indicates 5'-guanylic acid disodium salt.

In consideration of the above results of Examples 1 to 4 and Comparative Example 1 and preliminary tests if required, it could be understood that it is very easy for those skilled in the art to determine the composition of a feed solution suitable for depositing I+G mixed crystals having a target composition (I/G ratio).

Effect of the Invention

According to the present invention, the I/G ratio of mixed crystals of 5'-guanylic acid disodium salt and 5'-inosinic acid disodium salt can be controlled easily, and physical properties such as a specific volume, an angle of repose, and the like of crystals, particularly those of 5'-GMP2Na, can be improved easily.

What is claimed is:

1. A method for producing mixed crystals of disodium 5'-guanylate and disodium 5'-inosinate which comprises feeding a mixed solution of disodium 5'-guanylate and disodium 5'-inosinate which solution will become supersaturated at the below-mentioned constant temperature, to a solution or slurry of disodium 5'-guanylate and disodium 5'-inosinate charged in a crystallization bath (lower-temperature bath) and kept at a constant temperature, whereby mixed crystals of disodium 5'-guanylate and disodium 5'-inosinate are deposited from the mixed solution of disodium 5'-guanylate and disodium 5'-inosinate.

2. The method of claim 1, wherein the ratio (weight ratio) of the disodium 5'-inosinate to the disodium 5'-guanylate in said mixed solution of disodium 5'-guanylate and disodium 5'-inosinate is at least 0.5.

* * * * *